United States Patent
Saxena et al.

(10) Patent No.: US 7,717,618 B2
(45) Date of Patent: May 18, 2010

(54) APPARATUS AND METHOD FOR HIGH RESOLUTION TEMPERATURE MEASUREMENT AND FOR HYPERTHERMIA THERAPY

(75) Inventors: Indu Saxena, Torrance, CA (US); Harold Mukamal, Laguna Woods, CA (US)

(73) Assignee: Optech Ventures, LLC, Torrance, CA (US)

( * ) Notice: Subject to any disclaimer, the term of this patent is extended or adjusted under 35 U.S.C. 154(b) by 1175 days.

(21) Appl. No.: 11/325,907

(22) Filed: Dec. 30, 2005

(65) Prior Publication Data
US 2007/0156212 A1   Jul. 5, 2007

(51) Int. Cl.
*G01K 3/00* (2006.01)
*G01K 11/00* (2006.01)
*G01K 13/00* (2006.01)
*G01J 5/00* (2006.01)
*A61B 5/00* (2006.01)

(52) U.S. Cl. .................. 374/137; 374/121; 374/131; 374/161; 702/130; 702/131; 702/134; 600/549

(58) Field of Classification Search ............ 374/137, 374/121, 131, 161
See application file for complete search history.

(56) References Cited

U.S. PATENT DOCUMENTS

| | | | |
|---|---|---|---|
| 5,007,705 A | 4/1991 | Morey et al. | |
| 6,072,922 A | 6/2000 | Albin | |
| 7,046,349 B2 | 5/2006 | Everall et al. | |
| 7,048,732 B2 | 5/2006 | Ellingsen | |
| 7,297,154 B2 * | 11/2007 | Tu et al. | 607/88 |
| 7,447,388 B2 | 11/2008 | Bates et al. | |
| 7,512,291 B2 | 3/2009 | Mendoza | |
| 2004/0113056 A1 | 6/2004 | Everall et al. | |
| 2005/0273090 A1 | 12/2005 | Nieman et al. | |
| 2005/0273091 A1 | 12/2005 | Booth et al. | |
| 2008/0119739 A1 | 5/2008 | Vardi et al. | |

OTHER PUBLICATIONS

Thursby G. et al.,Versatile fiber Bragg grating arrays for strain mapping and ultrasound Lamb wave detection.Proc.SPIE, 2006 vol. 6379, 63790F1-12, Publ Online: Oct. 10, 2006.

Udd, Eric. "Fiber Optic Smart Structures," Fiber Optic Sensors;1991; John Wiley & Sons; Chichester; pp. 439-467.

(Continued)

*Primary Examiner*—Gail Verbitsky
*Assistant Examiner*—Mirellys Jagan
(74) *Attorney, Agent, or Firm*—Lawrence S. Cohen

(57) ABSTRACT

An apparatus and method for increasing the resolution of a linear array of fiber Bragg gratings by applying a plastic coating having a high CTE over the optical fiber. Apparatus and method for determining the temperature of each of a succession of points along a tissue portion during hyperthermia treatment includes an optical fiber with a succession of closely spaced fiber Bragg gratings. Each grating is responsive to a different wavelength and is sensitive to ambient temperature to change that wavelength as a function of temperature. A tunable laser operative continuously over a range of wavelengths including those to which the gratings respond is used to interrogate the gratings. Sensitivity-enhancing coatings are used on the fibers and the lasers are tuned over very short time cycles.

1 Claim, 10 Drawing Sheets

OTHER PUBLICATIONS

Astrahan, M. A., et al. "The accuracy of temperature measurement from within an intersitial microwave antenna," Int. J. Hyperthermia; 1988; vol. 4, No. 6; pp. 593-607.

Davis, M. A., et al. "Interrogation of 60 fibre Bragg grating sensors with microstrain resolution capability," Electronics Letters; Jul. 18, 1996; vol. 32, No. 15; pp. 1393-1394.

Davis, M.A. and A.D. Kersey. "Strain using fibre Bragg gratings and Brillouin scattering," IEE Proc.-Optoelectron.; Jun. 1997; vol. 144, No. 3; pp. 151-155.

Morey, W. W., et al. "Multiplexing fiber bragg grating sensors," Distribute and Multiplexed Fiber Optic Sensors; 1991; SPIE; vol. 1586; Bellingham; pp. 216-224.

Udd, Eric. "Fiber Optic Smart Structures," Proceedings of the IEEE; Jun. 1996; vol. 84, No. 6; pp. 884-894.

Michie, C., et al. "Optical Sensors for Temperature and Strain Measurement," SPIE; vol. 2718; pp. 134-146.

Michie, C., et al. "Optical Fibre Sensors for Monitoring of Structures (OSMOS)", SPIE; vol. 2718; pp. 385-397.

Meltz, G. "Overview of Fiber Grating-Based Sensors," SPIE; vol. 2838; pp. 2-22.

Ovren, C., et al. "Fiber-Optic Systems for Temperature and Vibration Measurements in Industrial Applications," Optics and Lasers in Engineering; 1984; pp. 155-172.

Domanski, Andrzej W. and Tomasz R. Wolinski. "Fiber-optic liquid crystalline high-sensitivity temperature sensor," Fiber Optic and Laser Sensors VII; 1989; SPIE vol. 1169.

Wolthuis, R. A., et al. "Dev. of Medical Pressure and Temp. Sensors Employing Optical Spectrum Mod.," IEEE Trans. on Biomed. Eng.; Oct. 1991; vol. 38, No. 10; pp. 974-981.

Shenfeld, O., et al. "Silver halide fiber optic radiometry for temp. monitoring and control of tissues heated by microwave," Opt. Eng.; Feb. 1993; vol. 32, No. 2; pp. 216-221.

Wickersheim, Kenneth and Mei H. Sun. "Fiberoptic Thermometry and its Applications," J. Microwave Power; 1987; pp. 85-94.

Astrahan M. A., et al. "Microwave applicator for transurethral hyperthermia of benign prostatic hyperplasia," Int. J. Hyperthermia; 1989; vol. 5, No. 3; pp. 283-296.

Lam, D. K. W. and Garside, B. K. "Characterization of single-mode optical fiber filters," Applied Optics; Feb. 1, 1981; vol. 20, No. 3; pp. 440-445.

Kersey, A., et al. "High-resolution fibre-grating based strain sensor with interferometric wavelength-shift detection," Electr. Letters; Jan. 30, 1992; vol. 28, No. 3; pp. 236-238.

Astrahan, M., et al. "Heating char. of a helical micro. applic. for transurethral hyperth. of benign prostatic hyperplasia," Int. J. Hyperth.; 1991; vol. 7, No. 1; pp. 141-155.

Astrahan, M. A., et al. "Interstitial Temperature Measurements During Transurethral Microwave Hyperthermia," The Journal of Urology; Feb. 1991; vol. 145; pp. 304-308.

Takasaki, Seiichi. "Photorefractive Gratings for Temperature Measurement," Thesis for Rutgers University; Oct. 1194; New Brunswick.

* cited by examiner

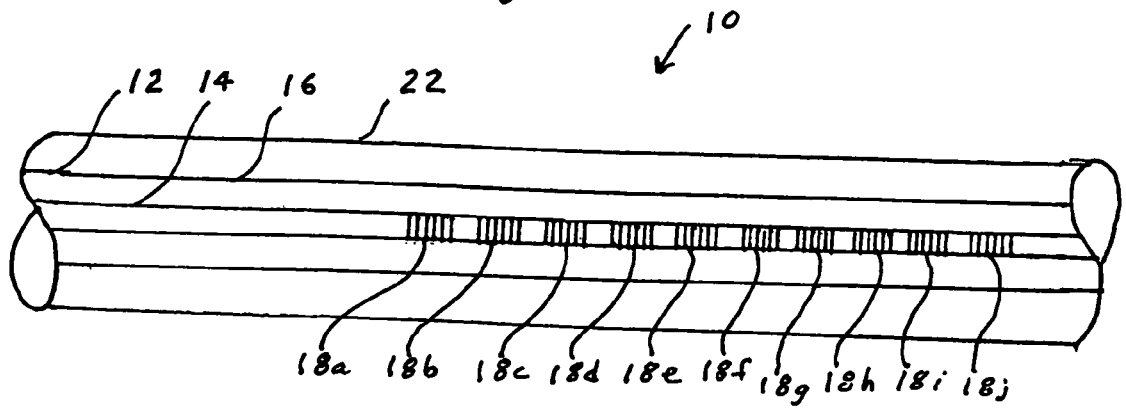
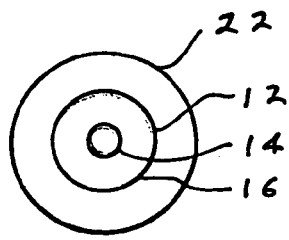
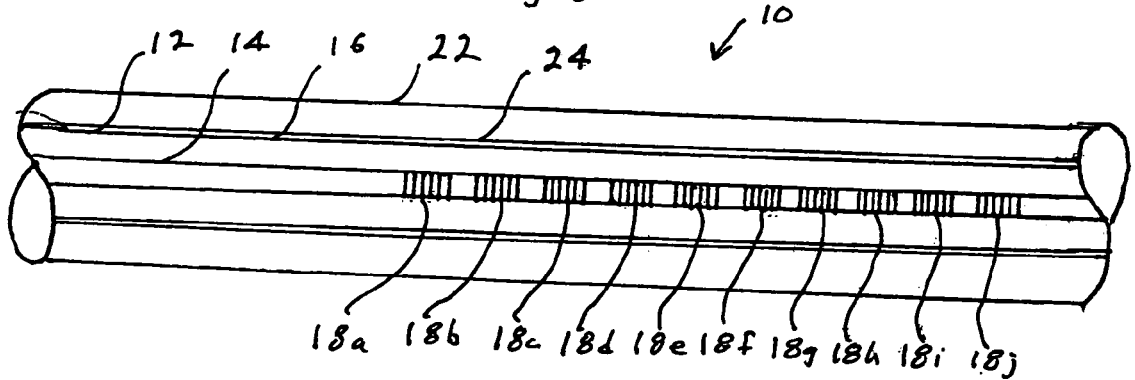
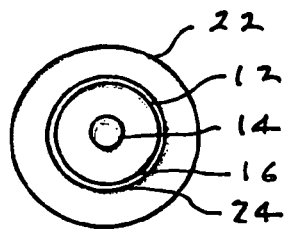

Temperature response plots of the 10 FBGs of the PMMA coated 10-sensor array

Wavelength resolution of optical fiber temperature sensor with sampling rates.

US 7,717,618 B2

APPARATUS AND METHOD FOR HIGH RESOLUTION TEMPERATURE MEASUREMENT AND FOR HYPERTHERMIA THERAPY

FIELD OF THE INVENTION

This invention relates to temperature sensing using fiber Bragg gratings in optical fibers.

This invention relates to fiber Bragg gratings in an optical fiber for measuring temperature in a series of closely spaced positions and more particularly to the closely spaced measurement of temperature of tissue exposed to hyperthermia therapy.

The invention also relates to on-line temperature profiling during hyperthermia therapy.

BACKGROUND

Sensing the value of environmental parameters such as temperature and strain using an optical fiber with a plurality of fiber Bragg gratings is known. For example in U.S. Pat. No. 4,996,419 there is disclosed for sensing strain a multitude of separate longitudinally spaced Bragg sensing gratings of substantially equal initial periodicity for all of the sensing gratings, each of the sensing gratings being situated at a different one of a multitude of separate locations.

During certain procedures, such as hyperthermia therapy a surgeon needs to know the temperature profile in the tissue at and near the area under treatment. A number of techniques and technologies are in use or being investigated for temperature sensing in conjunction with hyperthermia therapy. In one such technique the temperature at different locations is determined by inserting a cannula in the area under treatment, and by inserting a single point temperature sensor into the cannula. The point temperature sensor is moved within the cannula to different locations for reading temperature. Such a procedure is laborious, and of uncertain precision because of the need to relocate the point sensor for each measurement at each of closely spaced locations. Moreover, the temperature profile determined in this manner is not totally reliable and is not obtained simultaneously for the succession of locations. Another technique is the use of several point sensors separately connected and placed.

The need for temperature profiling occurs, for example, in cancer treatment when a tumor is to be heated during hyperthermia treatment. In this case, the tumor is to be heated, for example, in the range 41-45° C. (up to 113° F.), while the surrounding tissue is to be maintained at lower temperatures to avoid damaging healthy tissue.

Although hyperthermia therapy is under use and investigation for cancer, it is understood to be useful for other treatments. One such treatment is for BPH (benign prostatic hyperplasia).

As far as is known at present, different hyperthermia therapies employ different temperature ranges. For example, in investigational work with whole body hyperthermia a range of 40-42° C. is employed. In hyperthermia therapy to sensitize cancer cells to the effects of other therapies such as radiation therapy, chemotherapy and biological therapies, localized heating to temperature in the range of 41-45° C. have been used. Other techniques are used to achieve much higher temperature in order to ablate the tissue being treated. These techniques have been investigated in the brain, liver and prostate and require very precise placement of the energy in the tissue that needs to be ablated. In all types of hyperthermia therapy, temperature monitoring is critical.

Body tissue temperatures as high as 45° C. (113° F.) have been used in hyperthermia therapy. The effectiveness of hyperthermia therapy is related to the temperature achieved and other variables. In this regard it is important that the desired temperature is reached, but not exceeded. To accomplish this the temperature of the tumor or the area targeted for treatment and surrounding tissue most be closely monitored. Therefore accurate in vivo temperature monitoring is necessary, not only at the point or area under treatment but also at adjacent tissue. Also, for several of the heating methods, such as by microwave radiation, sensor immunity to electromagnetic fields is required. Consequently, it would be advantageous to provide a temperature profiling system and method that can measure temperature simultaneously (or nearly so) at a number of closely spaced locations, and that can do so repeatedly over short time intervals. Also, small changes in temperature should be made available over time intervals to measure change in temperature In certain hyperthermia applications the sensor must be able to measure discrete points over a short distance and the measuring points being as very close together. For example, the total distance may be 5 cm, with 10 measuring points. Typical hyperthermia treatment is applied to tissue areas spanning a length of about 1 cm-5 cm. Consequently in order to measure temperature at a plurality of point along such a distance very short fiber Bragg gratings must be employed. Also, in some hyperthermia applications it is desirable that each measuring point have a temperature resolution of at least 0.1° C. It is also desirable that the several measuring points provide sufficient spatial resolution that the temperature at one point does not overly influence the temperature reading at adjacent points, even if the measuring points are very close together. The invention in its various aspects and according to its principles address these requirements.

BRIEF DESCRIPTION OF THE DRAWINGS

FIG. 1 is a schematic drawing, not to scale, of an optical fiber having a linear array of FBGs and a plastic coating.

FIG. 2 is an end view of FIG. 1.

FIG. 3 is a schematic drawing, not to scale, of an optical fiber having a linear array of FBGs and a plastic coating and an area affected by use of an adhesion promoter between them.

FIG. 4 is an end view of FIG. 3.

DETAILED DESCRIPTION

Figure 5:
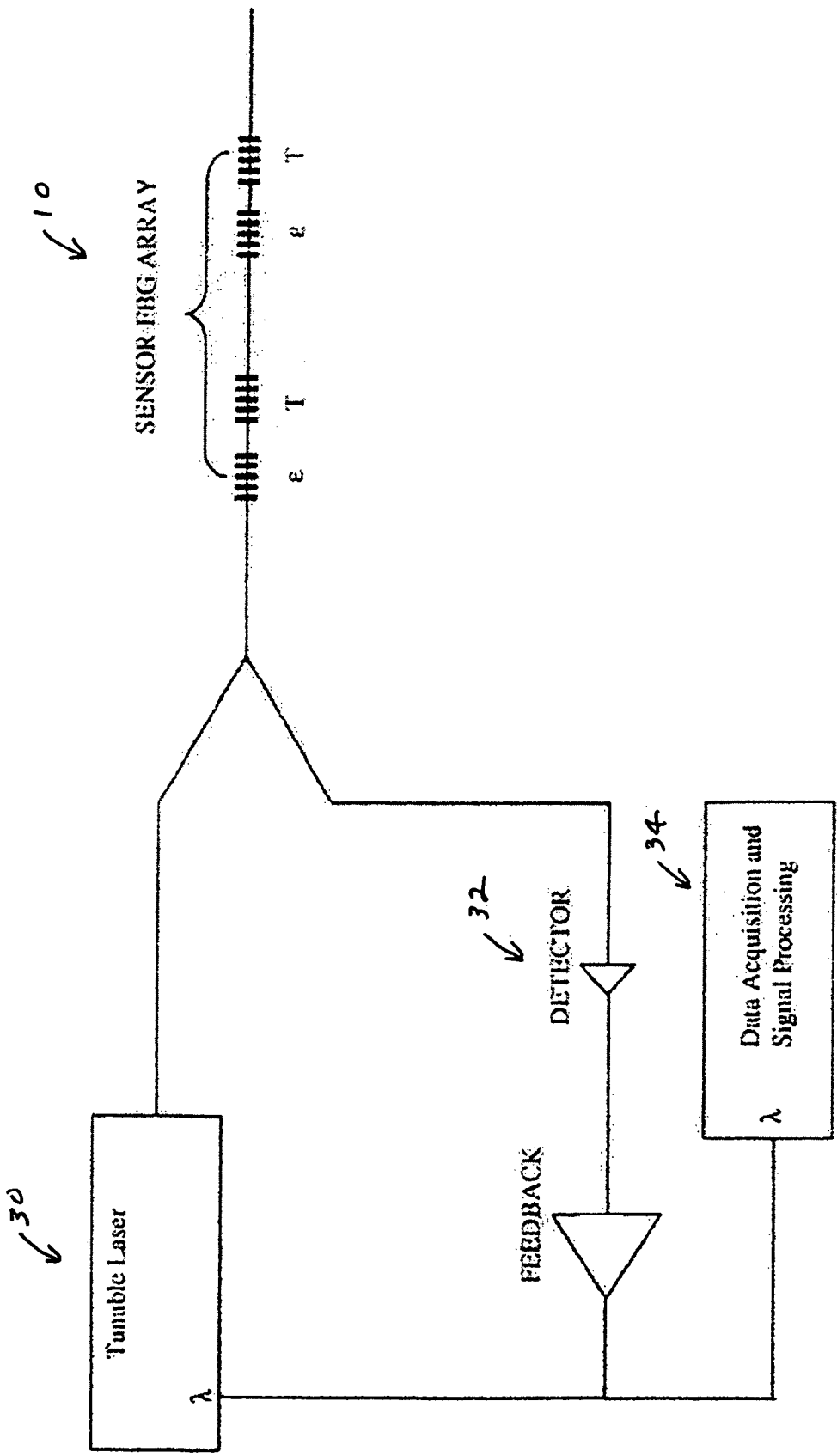
FIG. 5 is a schematic view of a system for use in the present invention.

In accordance with an aspect of this invention, a plurality of longitudinally spaced fiber Bragg gratings (FBGs) is formed on an optical fiber core. For purposes of this description the term "optical fiber" is taken to mean an optical fiber core and cladding, that is, the glass portion; unless the context requires a different meaning. It is also understood that FBGs are generally in the core portion. According to the invention, each of the plurality of FBGs is constructed to respond to a different reflection spectrum. Further, each FBG is operative to have a reflection spectrum that varies in a manner responsive to the temperature that is proximate to the FBG. Therefore, for a given state in which the temperature at each FBG is to be determined, each FBG will reflect at a different wavelength. Further, when the temperature changes proximate each FBG, the reflection spectrum shifts in response to the temperature changes imposed on the FBGs. Detection of the wavelength shift can be converted to temperature change based on a calibration. Since each FBG has a different reflection spectrum, the instantaneous reflection and the shift due to a temperature change, for each FBG can be discriminated from the others. In the prior art an FBG will give a reflection shift on the order of 0.1 nm/° C. due to change in temperature.

In the technology of FBGs, an FBG is defined as a periodic or aperiodic perturbation of the effective absorption coefficient and/or the effective refractive index of an optical waveguide. More simply put, a Bragg Grating can reflect a predetermined narrow or broad range of wavelengths of light incident on the grating, while passing all other wavelengths of the light. An FBG of the type under consideration here has an initial periodicity when it is created (called "writing"). The reflected wavelength at that initial periodicity at the time of fabrication of the FBG is referred to herein as the "specified Bragg wavelength" or the "specified characteristic peak wavelength". For purposes of this description those terms are used as in the technology but limited to the initial conditions at fabrication of the FBG. Those terms are considered inapplicable to detected spectral plots that are resolved sufficiently for the purposes of the invention because the spectral plot is too indistinct to define a peak. As will be seen below, in application of the present invention to obtain high temperature resolution, it has been found that the spectral plot at any given time does not exhibit a sufficiently distinct peak to allow for providing as output the needed resolution. Consequently such a reflection cannot be said to have a characteristic peak until additional processing is carried out. That additional processing will be described below.

A goal of the present invention is to provide a much greater reflection shift per degree change in temperature, Kt, and as will be seen, this can be accomplished with the present invention on the order of 50 pm/° C. By this means much smaller changes in temperature can be measured.

It is understood under specified conditions the wavelength separation of FBGs is determined by the formula Kt×Tr+X where Kt is the desired change in reflected wavelength per unit temperature, Tr is the expected or desired maximum temperature range, and X is any expected wavelength change induced by non-thermal effects. Consequently as the desired Kt goes up for a given temperature, the wavelength separation, must also increase. And conversely, as Kt goes down, the wavelength separation can decrease. The temperature range for these purposes is defined as starting at the temperature of fabrication of the FBGs to the maximum temperature to be measured.

This is accomplished by coating the optical fiber with a non-conductive, preferably plastic, material having a coefficient of thermal expansion (CTE) much greater than that of the optical fiber.

It is a further goal of the present invention that by forming the FBGs sufficiently close together and sufficiently small enough to respond to the temperatures of tissue spaced over the selected distance, a temperature profile can be produced without the laborious repositioning necessitated by a point sensor apparatus of the prior art, or with a plurality of separate point sensors placed at selected places as for hyperthermia applications.

In order to obtain accurate temperature readings from a fiber, so constructed, a wavelength-tunable light source that tunes over a wavelength range in a given time interval is used. A sampling rate of the returned signal must then be applied sufficient to provide the needed resolution data. In addition, robust software algorithms are used to perform peak searches to construct peak locations for the FBG reflection spectra at each measurement cycle. The algorithms provide thresholding, binning, curve smoothing and curve fitting as are all described below.

To this end, apparatus, in accordance with this invention, includes a tunable laser, which changes the output wavelength as a function of time over a selected wavelength range. The reflected light from the FBG is incident on a photodetector, as the wavelength is swept and thereby, by repeated cycles, makes a wavelength change measurement as a function of time at the selected sampling rate. The system is calibrated to a base wavelength/temperature equivalent, thereby allowing each reflected wavelength to be converted to a temperature measurement; and repeated cycles to output change in temperature over time.

The present invention, in one aspect, provides a new and improved system and method for measuring temperature at a plurality of points by use of a plurality of FBGs linearly spaced on an optical fiber.

In a particular aspect the system and method of the invention provides improved temperature sensitivity, for example responding to and allowing measurement of temperature changes at least as small as 0.1° C., and possibly as small as 0.02° C. As will be explained in detail below this is accomplished by surrounding the optical fiber with a coating that has a CTE greater than that of the optical fiber.

In another particular aspect the system and method of the invention provides much smaller spatial resolution than was previously available, for example the space between adjacent FBGs or the spatial resolution of the temperature measurement can be as small as 1 mm. If the FBG can be constructed with a length of about 5 mm, then for a sensor having a total length of about 50 mm as many as 10 sensor sites can be created.

In another aspect, the system and method of the invention is for temperature measurements as part of apparatus for and in the process of hyperthermia therapy.

In another aspect, it is recognized that the short FBGs necessary for placing them over a short distance do not exhibit a sufficiently precise peak wavelength for the accuracy needed for very small temperature differences. Therefore a curve fitting and smoothing procedure is applied.

For use in detecting and monitoring temperature changes as a profile along a distance a plurality of FBGs can be spaced apart along a selected length of optical fiber.

One aspect of the invention is a temperature sensor having a plurality of fiber Bragg gratings spaced apart in the optical fiber-, in which increased sensitivity to temperature changes can be achieved by coating the optical fiber with a material that has a coefficient of thermal expansion higher than to that of the optical fiber. This aspect is more particularly defined as using a non-conductive coating so that it can be applied to usage where an electromagnetic field is present whereby the non-conductive coating does not respond to or cause a variation in the electromagnetic field. Use of a non-conductive coating is particularly useful for hyperthermia therapy in which microwave energy is used.

Another aspect of the invention is a temperature sensor as described above in which the plurality of FBGs are interrogated in timed cycles (scanning rate) in order to obtain changes in temperature at each FBG location and thereby changes in the temperature profile. In the context of hyperthermia therapy it is necessary to detect very small changes in temperature at each location of an FBG, such as at least 0.1° C. It is also important to obtain very accurate spatial resolution of temperature measurement, that is the number of measurement points, by making the length of the FBGs as small as possible over the desired distance for creating the temperature profile. The distances over which temperature profiling for hyperthermia therapy is required are very short ranging from about 2 cm to about 5 cm. This is especially a problem where the number of measurement points required may be as many as 10, over a 5 cm distance. In order to place 10 FBGs in a distance of about 5 cm, each FBG must be very short. However as FBGs are shortened, their reflection spectra at any given set of parameters broadens from a sharp peak to a broad "top hat" form along with considerable side lobes. Thus, when the requirement is at once to obtain very precise spatial separation of closely spaced measuring points coupled with the requirement for very precise temperature sensitivity; a system is required that can both obtain the required temperature sensitivity and spatial discrimination and discriminate the data obtained from reflection spectra that are imprecise.

In the preferred embodiments of the invention a resolution of at least 0.1° C. is desired. A plastic coating of the optical fiber having a CTE of at least twice that of the optical fiber enables this resolution. However, in the preferred embodiment, an indistinct peak of the spectral plot of a reflected FBG signal is caused by the short length of the FBG coupled with the need to resolve the spectral plot to an accuracy of about 0.1° C. Where short FBGs such as about 5 mm or less are employed, in order to detect and provide an output of the desired resolution it is necessary to apply the desired sensitivity range or specification, Kt, a sufficiently large sampling rate and a peak detection algorithm.

The preferred coating CTE is at least about $2 \times 10^{-6}$ and for hyperthermia applications, at least about $10 \times 10^{-6}$.

Figure 13:
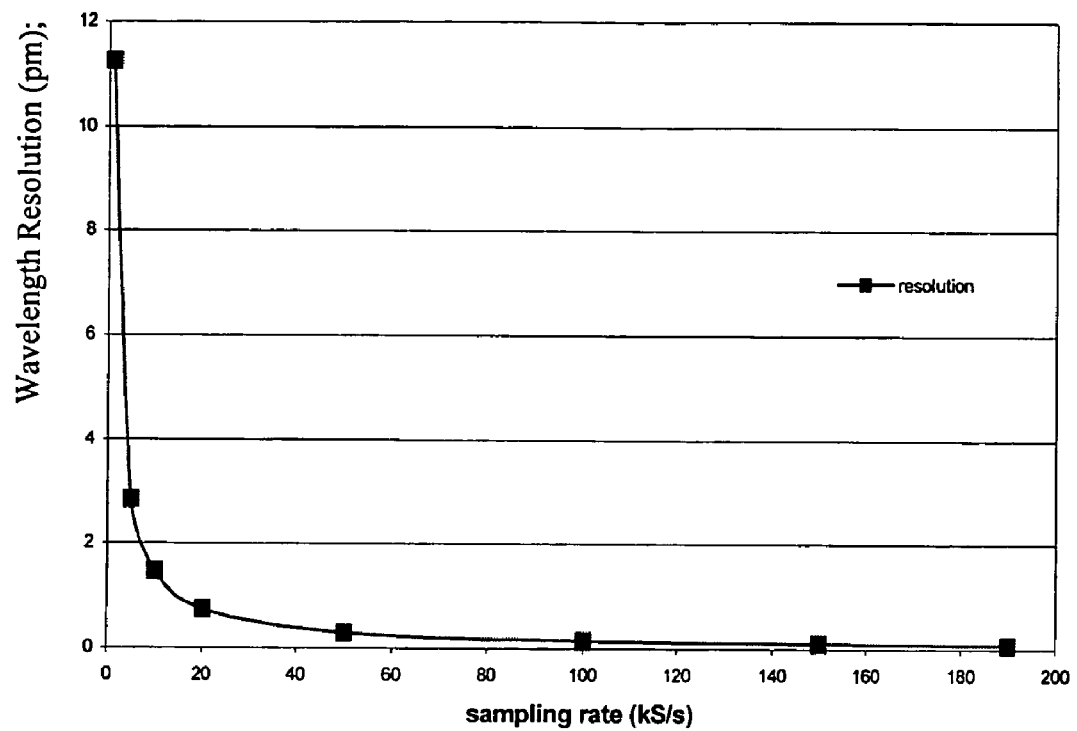
FIG. 13 is a plot showing the variation of sensor resolution with sampling rate.

Sampling rates of from about 5 kS/s to about 100 kS/s are preferred (above this rate improvement of the resolution is insignificant). This can be seen in FIG. 13.

Temperature Sensor

FIGS. 1 and 2 show a temperature sensor 10 having an optical fiber 12 having a core 14 and a cladding 16 in which a series of 10 fiber Bragg gratings (FGBs) 18a, 18b, 18c, 18d, 18e, 18f, 18g, 18h, 18i, and 18j (shown schematically) are spaced apart in the fiber core 14. The temperature sensor 10 has a non-conductive coating 22 in mechanical contact with the optical fiber 12.

The non-conductive coating 22 has a coefficient of thermal expansion (CTE) substantially greater than that of the optical fiber, in the range of at least about twice that of the optical fiber. Preferably the CTE of the coating is at least about 10 times that of the fiber. Further preferably, the CTE of the coating is in the range of at least about $2 \times 10^{-6}$/° C. and up, and for hyperthermia applications, preferably from at least about $10 \times 10^{-6}$/° C. For applications in an electromagnetic field environment, the coating 22 is a non-conductive material such as a plastic material formed around the fiber. The coating will be applied over the optical fiber after the FBGs have been formed. In the case of a polymeric non-conductive plastic material, it will be applied and cured over the fiber.

As will be seen, the temperature sensor 10 functions to increase the temperature sensing sensitivity of the FBGs by means of the coating expanding or contracting due to temperature change and thereby straining the FBGs. The strain on the FBGs changes their reflection spectra and detection of a peak wavelength of the reflection spectra is used along with a correlation function to determine the temperature or the change in temperature as related to a base or series of prior measurement cycles.

Three factors influence the precision of temperature measurement and the very small temperature resolution according to the present invention. These are:

The thermo-optic effect by which the index of refraction of the glass changes with temperature;

The change in length of the glass with change in temperature, which acts upon the FBGs to shift the reflection spectrum;

The strain effect on the FBGs caused by the much greater expansion and contraction of the coating causing a shift in the reflection spectrum.

The first two of these effects in a typical FBG allows on the order of 0.1 nm change in reflected wavelength per 10° C. However in order to be able to detect temperature measurement on the order of 0.1° C., it is necessary to be able to read on the order of 0.001 nm, that is 1 pm, change in the reflected wavelength in the FBGs and the present invention provides this level of resolution and detection of temperature change.

A number of factors make this possible. One of these factors is the quality of the contact between the coating 22 and the optical fiber 12. A more firm or stronger contact will result in greater translation of the expansion or contraction of the coating into strain of the optical fiber resulting in a greater shift of the reflection spectra of the FBGs. In other words, for say 0.1° C. change in temperature, the coating expands (or contracts) more than would the optical fiber alone due to its higher CTE, and to the extent that greater temperature response is transmitted as more strain on the FBG, higher resolution is possible.

FIGS. 3 and 4 show an alternative embodiment in which the temperature sensor 10 has the FBGs 18a-18j as in the previous example. In this case however an intermediate material 24 is in place between the optical fiber 12 and the coating 22. The intermediate material 24 is a material that will increase the mechanical connection of the coating 22 and the optical fiber 12. It could be an adhesive or an adhesion promoter or other material that will bond to both the coating 18 and the fiber 12. Silane adhesion promoters are especially applicable.

In operation the temperature sensor when exposed to temperature variation will experience a degree of change in thickness and length (expansion or contraction) of the coating that will impose a radial and axial force (tension or compression) on the fiber 12, seen as strain on the FBGs. The change in temperature is also experienced in the fiber 12 itself resulting in a component of the spectral shift of the FBGs; but the use of the high CTE coating, by translating its higher thermal response to temperature change to a mechanical force on the fiber, causes a much greater effect on the FBGs. This much greater effect is defined herein as thermal force strain amplification on the fiber 12. That increase in strain per ° C. results in a greater wavelength shift per ° C., consequently, greater sensitivity. The sensitivity to temperature change in an optical fiber, in terms of wavelength shift per ° C., Kt, without the benefit of the present invention is typically in the range of 9-10 pm/° C. With the non-conductive plastic coating of the preferred embodiment of the present invention, Kt is seen to increase to the level of 50-55 pm/° C.

Consequently, the shift in the reflection spectra of the FBGs is much greater than in the case in which the thermal effect is only that of the optical fiber itself. Coatings that have been used are polyethylene, polypropylene, polymethylmethacrylate, polytetrachloride, polystyrene and polytetraflouroethylene (Teflon) and polyamide.

With the described structure of the sensor, much greater sensitivity to temperature change can be transmitted from the FBGs. Temperature change as small as 0.1° C. or even smaller; in theory, as small as 0.02° C. can be detected.

Non-conductive polymeric materials that have CTE levels 5 or more times that of the optical fiber material are considered suitable for the coating in hyperthermia therapy applications.

In most cases the coating's CTE falls off at temperature over its glass transition temperature ($T_g$). Consequently such plastics should be used only in temperature ranges below the $T_g$. However some materials do not follow that condition, and can be used even above their $T_g$. The following materials have sufficiently high CTEs in the order of tens to 100 times that of fused silica that they are considered applicable for use in constructing the sensor; polyvinylchloride (both below and above its $T_g$), polymethylmethacrylate (PMMA), polystyrene, polytetrachloride, polyacrylonitrile, polyethylene, polypropylene, polytetraflouroethylene and polyamide.

For medical hyperthermia therapy purposes heating to a temperature range of 40-55° C. is desired; except that for ablation therapy higher temperatures are used. Use of a polymer coating with a CTE in the above temperature range has been shown to increase the temperature response of FBGs from the nominal value of standard telecommunication grade fiber of 0.01 nm/° C. to at least 0.05 nm/° C.

For purposes of the present invention it is preferable that the FBG array have a collective reflection spectrum from about 1220 nm to about 1680 nm. In a case as illustrated in which the FBG wavelength separation is as much as 3.5 nm, a collective reflection spectrum of 35 nm is adequate, suggesting that a range of from 1540 nm to 1580 nm is adequate. In addition, the tunable laser scanning range that is available is from 1500 nm to 1600 nm.

Test and Result

Test 1

A high sensitivity germanium doped single mode fiber that is hydrogenated at a temperature of 80° C. and pressure of 600 psi was used to write 10 FBGs to fabricate a 10 point temperature sensor. The fiber parameters are:

Fiber (cladding) diameter=125 μm, core diameter 9.8 μm, numerical aperture 0.13, cutoff wavelength 1213 nm, index of refraction (n) approximately 1.46. The fiber used was Fibercore PS1500.

The FBGs were written into the fiber, each being 5 mm long separated by 0.02 mm and corresponding to FBG wavelengths separated by 3.5 nm, as follows:

| | Bragg Wavelength (nm) |
|---|---|
| 1 | 1548 |
| 2 | 1551.5 |
| 3 | 1555 |
| 4 | 1558.5 |
| 5 | 1562 |
| 6 | 1565.5 |
| 7 | 1569 |
| 8 | 1572.5 |
| 9 | 1576 |
| 10 | 1579.5 |

This sensor array was dip coated in polymethylmethacrylate (PMMA) (high molecular eight 18,226-5 from Sigma Aldrich) dissolved in chloroform, to a thickness of about 0.9 mm, and cured under high temperature in a vacuum oven.

In each case the sensor was placed inside a plastic tube of 3 mm inner diameter and immersed in a water bath. The bath temperature was started at 65° C. allowed to cool. The temperature of the water was varied from 65° C. to 25° C. The temperature response was obtained at intervals.

The reflection spectra of the 10-sensor array was measured by a high speed tunable laser based detection system. The tunable laser system for reading the reflection spectra is shown in FIG. 5 showing a sensor 10, a tunable laser 30, a wavelength selective dector 32 and a specially programmed processor 34.

Figure 6:
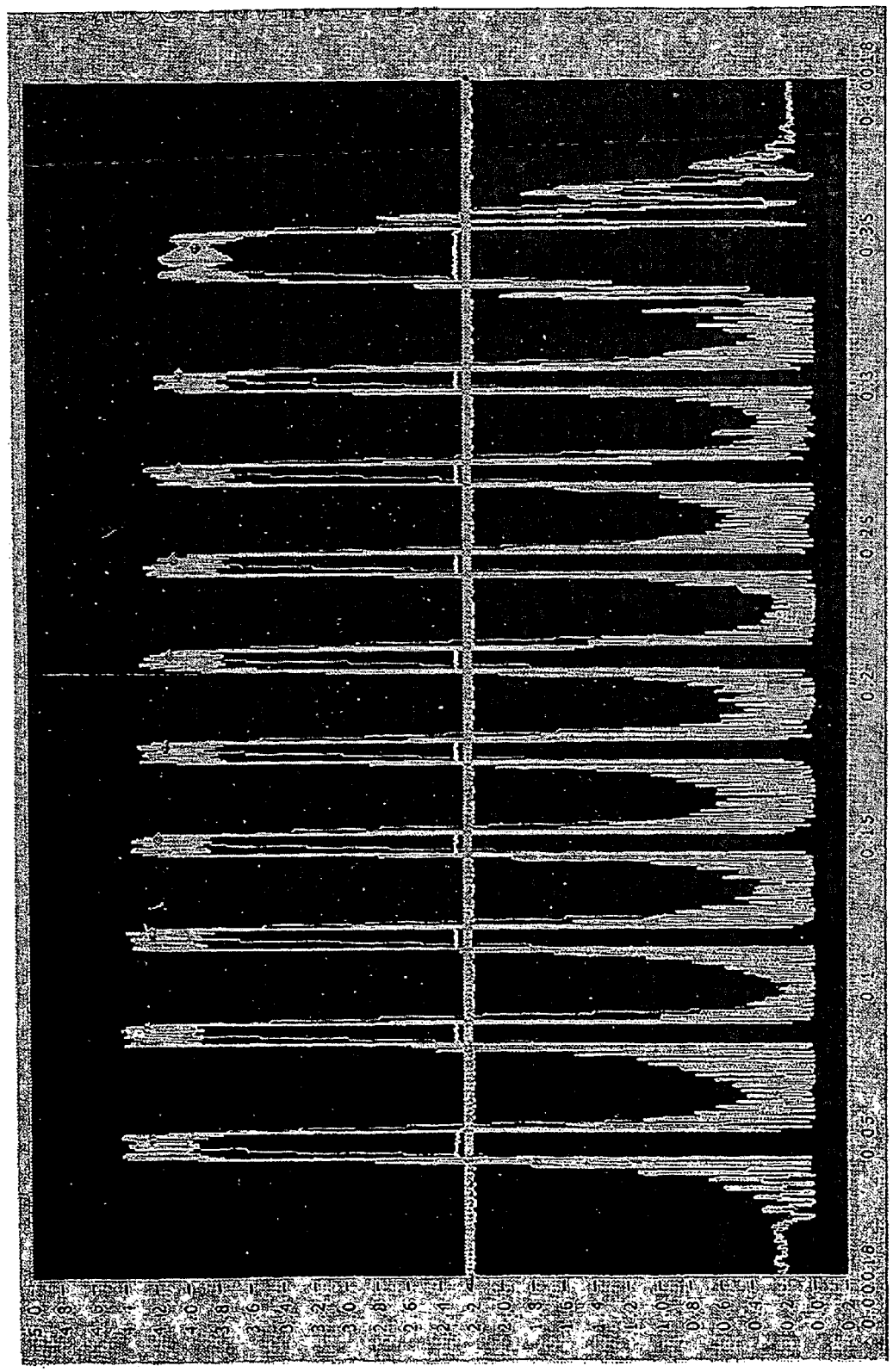
FIG. 6 is a spectral plot of reflection spectra from FBGs according to the present invention.

A spectral plot of the reflection spectra from one measurement of this test is shown in FIG. 6. This spectral plot was made with a scanning rate from the tunable laser light source 30 to 100 nm/s. The sampling rate of the detector 32 was 60 kS/s. This spectral plot shows indistinct peaks when the interrogation is at a high scanning rate over the wavelength range.

Figure 7:
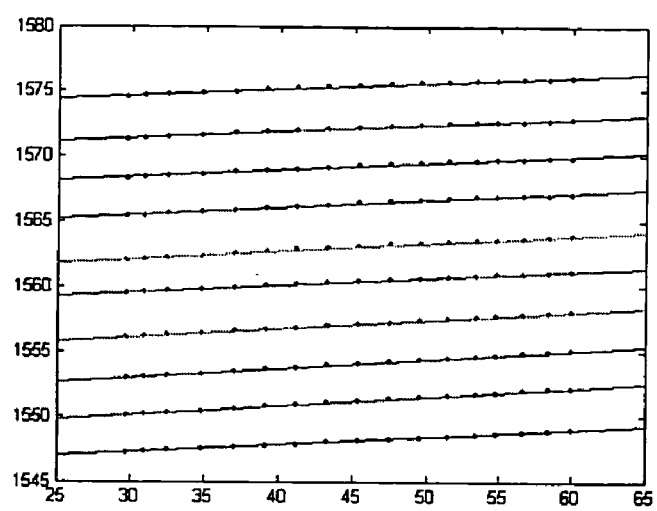
FIG. 7 is a temperature response plot 10 FBGs of a PMMA coated 10 sensor array.

The 10 different values of dλ/dT (Kt) are for each 5 mm location of the FBG, corresponding to the slope of each FBG response on the plot of FIG. 7. The baseline temperature $\lambda_o$ is 0° C. The Kt's are all approximately (actually greater than) 50 pm/° C. that is the response required to obtain the 0.1° C. temperature resolution.

The slope of each curve, which defines Kt is shown below.

| dλ/dT (nm/° C.) | $\lambda_o$ (nm) |
|---|---|
| 0.05667 | 1545.5 |
| 0.07075 | 1548.0 |
| 0.06980 | 1550.9 |
| 0.06338 | 1554.2 |
| 0.05412 | 1557.9 |
| 0.05941 | 1560.4 |
| 0.05669 | 1563.8 |
| 0.05201 | 1566.8 |
| 0.04898 | 1569.9 |
| 0.4629 | 1573.3 |

In order to resolve the indistinct peaks, a set of peak detection and calibration algorithms is employed. This is described in detail below. After application of the algorithms, the spectral plots will have a fitted curve from which a peak can be derived (see FIG. 12).

A second sensor array was prepared in the same way but was not coated.

Figure 8:
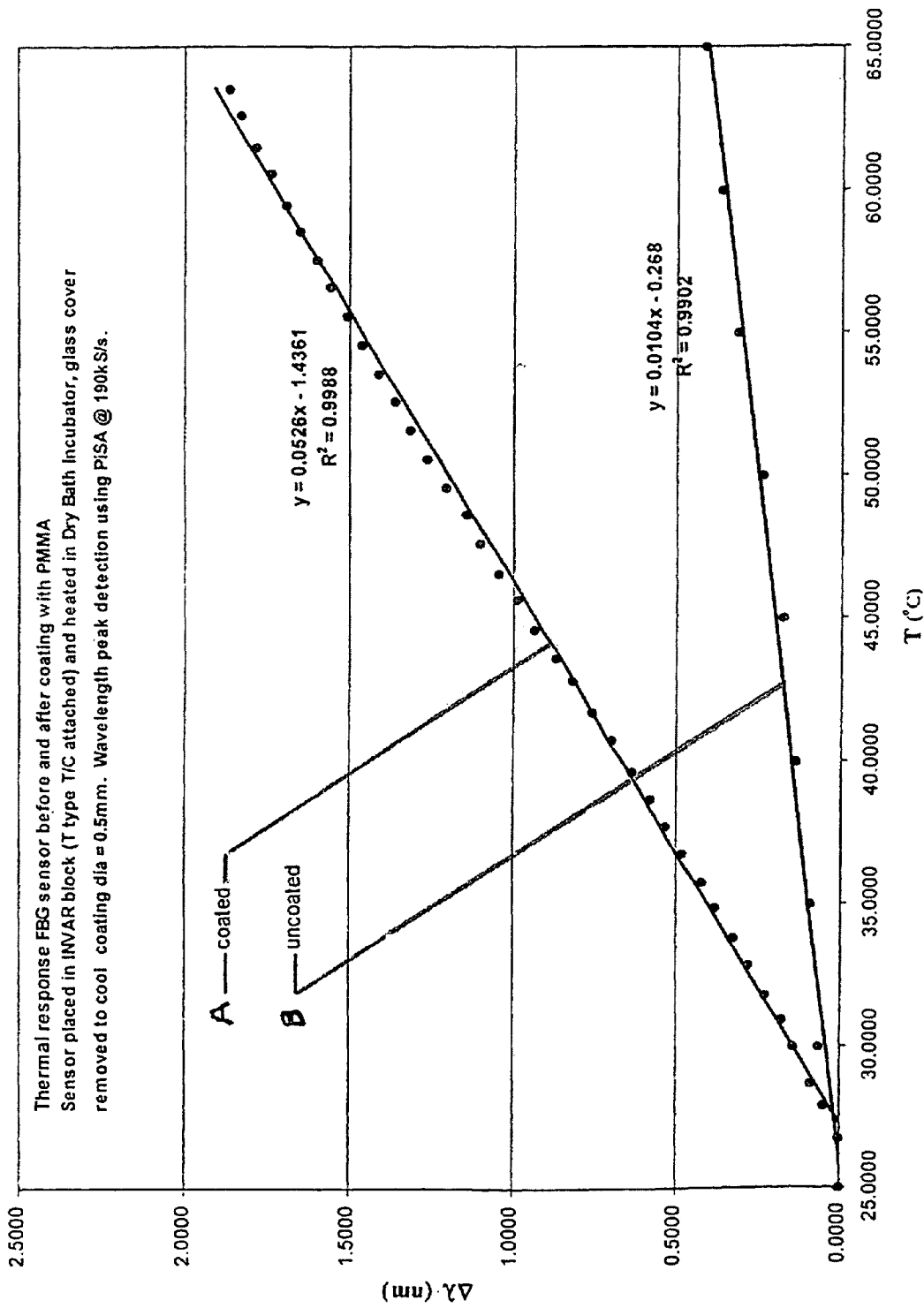
FIG. 8 is a comparative plot of temperature response of a PMMA coated FBG and an identical uncoated FBG.

A selected one of the FBGs in the coated and uncoated arrays were tested for thermal response. The tunable laser was used as the interrogating source. The reflected light was directed to the detector and processed to determine the wavelength shift for each specimen as the temperature was increased. The results are shown in FIG. 8 in which line A shows the response from the specimen coated with PMMA and fine B shows the response for the uncoated specimen. The response lines demonstrate that the PMMA coated specimen had a temperature sensitivity on the order of 5 times that of the uncoated specimen. That is, Kt for the uncoated sensor was 0.0104, while for the coated sensor Kt was 0.0526

Test 2

Figure 9:
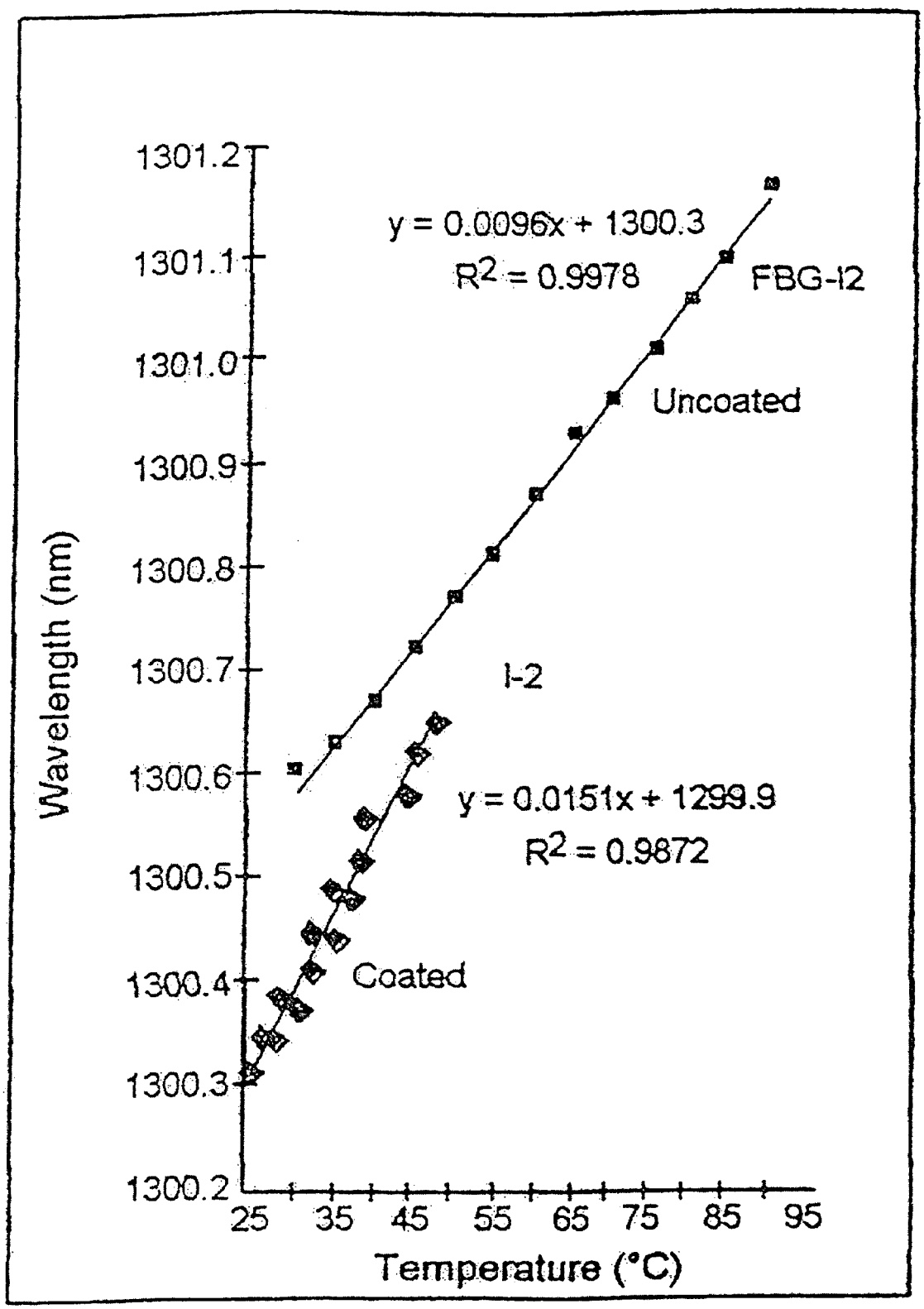
FIG. 9 is a comparative plot of temperature response of a polyethylene coated FBG and an identical uncoated FBG.

In another test the coating was polyethylene. The two specimens were prepared and the test conducted and the results processed in the same way as for Test 1. The results are shown in FIG. 9. The response lines demonstrate that the polyethylene coated specimen had a temperature sensitivity Kt on the order of 1.57 times that of the uncoated specimen.

Test 3

Figure 10:
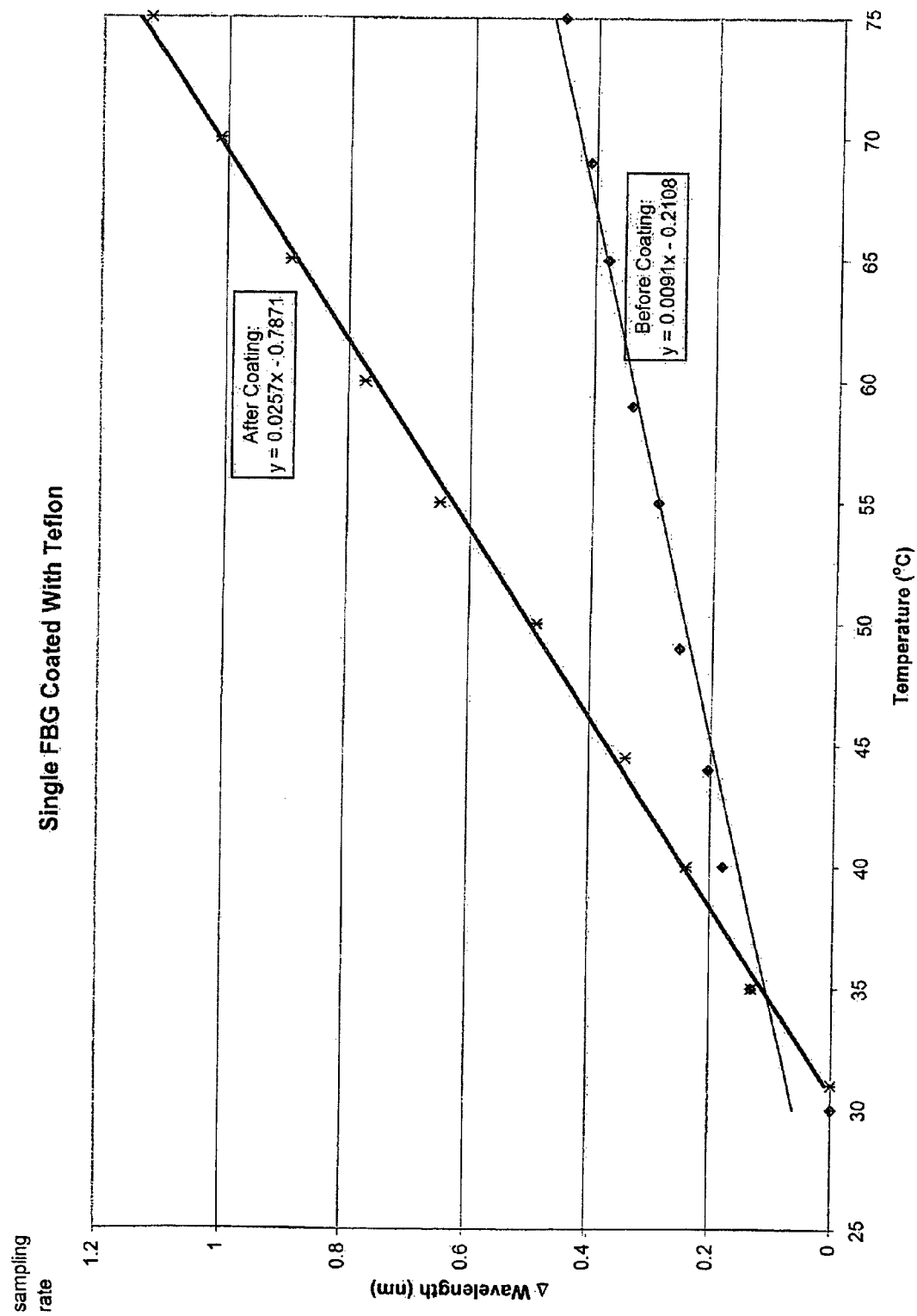
FIG. 10 is a comparative plot of temperature response of a Teflon coated FBG and an identical uncoated FBG.

In another test the coating was polytetraflouroethylene (Teflon). The two specimens were prepared and the test conducted and the results processed in the same way as for tests 1 and 2. The results are shown in FIG. 10. The response lines demonstrate that the Teflon coated specimen had temperature sensitivity on the order of 2.8 times that of the uncoated specimen.

Detection System

Figure 11:
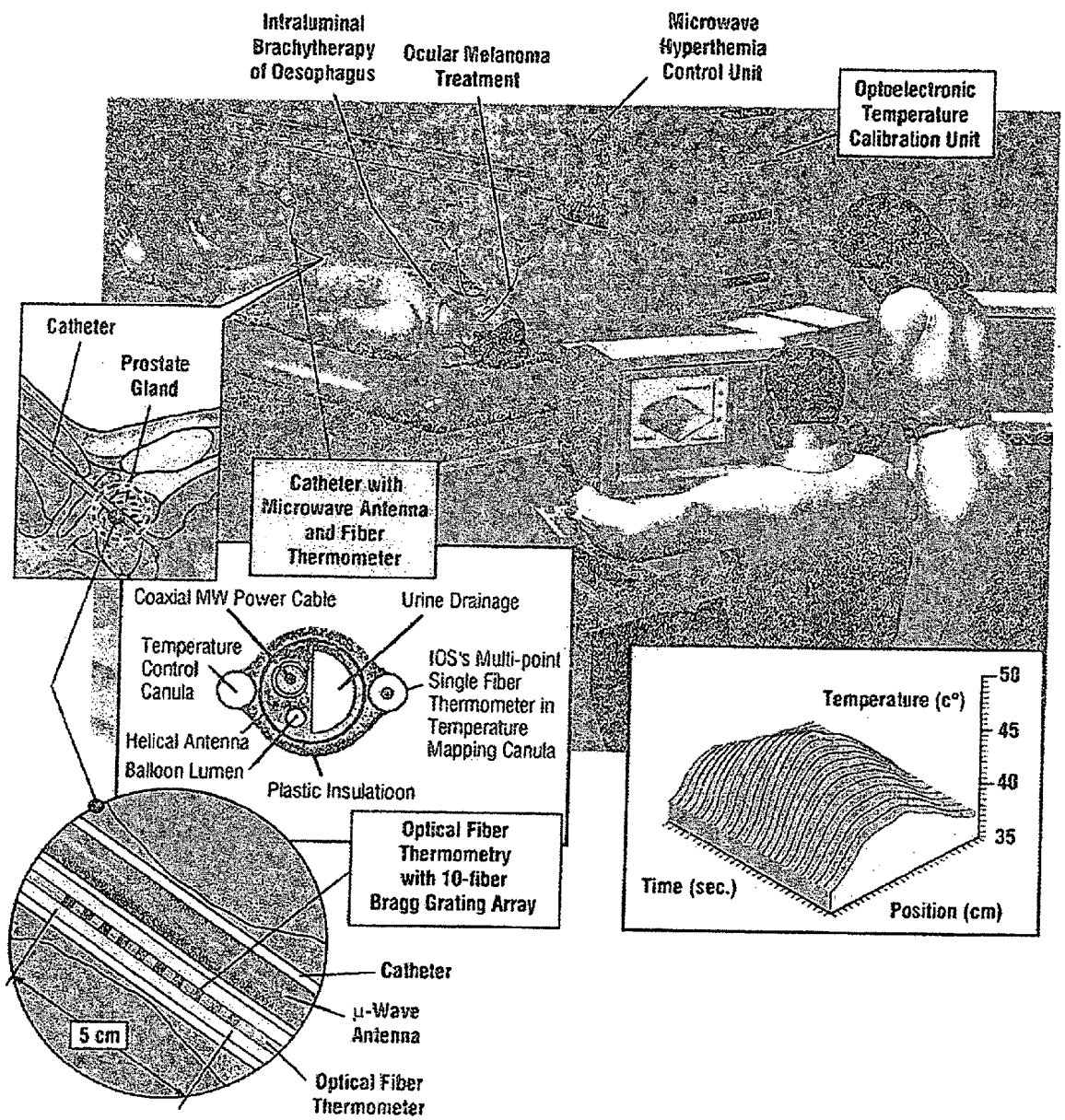
FIG. 11 is a picture of a system in use for hyperthermia therapy using the present invention.

FIG. 11 shows the system that embodies the system aspect of the invention in the hyperthermia context in which a catheter has a temperature sensor (optical fiber thermometer) comprising a series of FBGs on an optical fiber. In considering this system description in the hyperthermia context it is appreciated that the system can be applied mutatis mutandis to other applications.

All surgical procedures incorporate some degree of risk, and may cause physical, financial and even psychological distress to a patient and the patient's family. This is particularly true in the case of prostate problems because the results of surgery can seriously affect a man's quality of life. Because of these risks, less destructive and less invasive, but effective, alternatives have been the subjects of extensive research and increased use. Among these alternatives, microwave hyperthermia has been clinically proven to be an effective, efficient and non-toxic method for treating tumors. Unfortunately its use has been limited by the lack of an effective tool to monitor and thereby control the amount of heat distribution during microwave treatment of tumors. This has been a problem both respecting the amount of heat and its exact location and distribution in the human organ under treatment. One problem in particular is the need to measure temperature and temperature change over short distances and with very high accuracy.

The present invention is a temperature sensor and an associated system that can be used in-vivo in conjunction with therapeutic heat application such as hyperthermia, including microwave therapy. The invention is a temperature profiling sensor that senses temperature and temperature change along a short distance adjacent or within an animal organ; and that can do so with a very high degree of sensitivity for temperature change.

The sensor can be implemented in one example to measure multiple points along a 5 to 10 cm sensor length, with the ability to pinpoint target areas within 0.5 cm. It can also be implemented to monitor temperatures over a large range at each sensing point, including the range desired for microwave hyperthermia of 35° C. to 55° C. with a 0.1° C. temperature resolution. These measurements can be accomplished with the invention with no cross sensitivity to microwave self-heating. The invention is implemented with a single mode or multi-mode optical fiber with a specially defined coating as described above. It will readily interface with clinical hyperthermia catheters.

In the particular application for hyperthermia the sensor will provide an axial arranged array of FBGs, each being 0.5 cm long that will provide high sensitivity (better than 0.5° C.), high accuracy (0.1° C.) and accurate spatial resolution (0.5 cm) in a single optical fiber. Distributed thermometry is accomplished remotely, using an optoelectronic module that will measure temperature induced wavelength shifts of the Bragg wavelengths.

| FBG | Thermal Response Change of 10 Sensor Array Upon Coating with PMMA | |
|---|---|---|
| | Bare Uncoated Sensor Temperature Response, Kt (pm/° C.) | Coated Sensor Temperature Response, Kt (pm/° C.) |
| 1 | 11.0 | 41.4 |
| 2 | 10.3 | 41.8 |
| 3 | 9.4 | 40.2 |
| 4 | 9.3 | 39.8 |
| 5 | 9.2 | 40.4 |
| 6 | 9.7 | 38.9 |
| 7 | 9.6 | 39.2 |
| 8 | 10.6 | 42.3 |
| 9 | 11.9 | 38.3 |
| 10 | 8.8 | 25.8 |

As already noted, it is desirable to obtain temperature changes at a level of at least 0.1° C., and, as well, temperature reading to an accuracy of at least 0.1° C. in FBGs that are used in an array over such a short distance that the FBGs have to be quite short themselves. This is particularly the case in hyperthermia treatment. However when attempting to resolve the reflection spectra of such short FBGs to the precision that will give such sensitivity, the peak of the reflection spectra is too indistinct, as shown in FIG. 6.

The following described aspect of the invention is directed at solving that problem. In this description, reference is made to the system of FIG. 5.

A temperature sensor having sufficient resolution to detect changes in temperature of 0.1° C. or better is needed. One such temperature sensor is that shown and described above.

The temperature sensor 10 is interrogated by a scanning light source as exemplified by a tunable laser scanning light source 30 having a scanning wavelength range sufficiently broad to cause reflection from all the FBGs and operating at a selected or otherwise set scanning rate.

Reflections from the FBGs are sent to the wavelength selective detector 32 that operates at a sampling rate that is selected or set, preferably by a specially programmed processor. The detector converts the reflected light signals from the FBGs to electrical changes varying in time that is converted to wavelength.

The reflected lights signals are in a form as seen on FIG. 6 which is so finely resolved that there is no distinct peak. The following described process is used to define peaks for the reflected signals from each FBG. First it is necessary to have the specified characteristic peak wavelength (as defined above) for each FBG.

The processor is programmed with algorithms for detecting changes and defining peaks in the FBG reflected spectra including the steps of thresholding, binning, smoothing and least squares fitting.

A major constraint is that the peaks must be spaced such that the bins do not overlap. If the bins overlap, more than one peak per channel could be detected, and incorrect shifts would be observed and recorded. In addition if a peak moves out of its predefined bin due to the applied temperature exceeding that accounted for in the pre-defined bin, the reflected signal will no longer be identified nor will its peak be detected to indicate the temperature of the location at which it exists Hence the size of the bin must be selected extremely carefully keeping all these factors in mind.

One aspect that affects the binning size is accomplished by selecting sufficient wavelength separation of the wavelength adjacent FBGs, which in turn is a function of the expected temperature range. In general if the desired Kt is lower, then the minimum wavelength separation between FBGs can be lower or conversely as the desired Kt is increased, the minimum wavelength separation between FGBs must be higher. For hyperthermia purposes having a temperature range of about 38° C. to about 45° C., a Kt of 20 pm/° C., a wavelength separation of 0.5 nm is considered as being the minimum. For procedures in which larger temperature ranges in particular, higher temperatures are expected such as ablation procedures, a wavelength separation of 3.5 nm is preferred assuming a Kt of 50 pm/° C. and a temperature range from room temperature (25° C.) to 100° C.

The sampling rate (data points/sec) is defined by $$\frac{\text{light source scanning rate (nm/sec)}}{\text{desired temperature resolution (deg C.)} \times Kt \text{ (nm/deg C.)}}.$$

In the system of FIG. 6 the sampling rate is applied to the wavelength selective detector 32.

False (additional) peaks can also be detected due to changing intensities of the side lobes of an FBG, where the side lobe peaks may increase above the pre-defined intensity threshold measurement during a measurement. This is remedied by implementing a least squares polynomial fit to the raw data of the entire FBG's spectral envelope for each reflection event. The peaks are fit to at least a second order polynomial. A LABVIEW curve-fit program has been used for this procedure.

Figure 12:
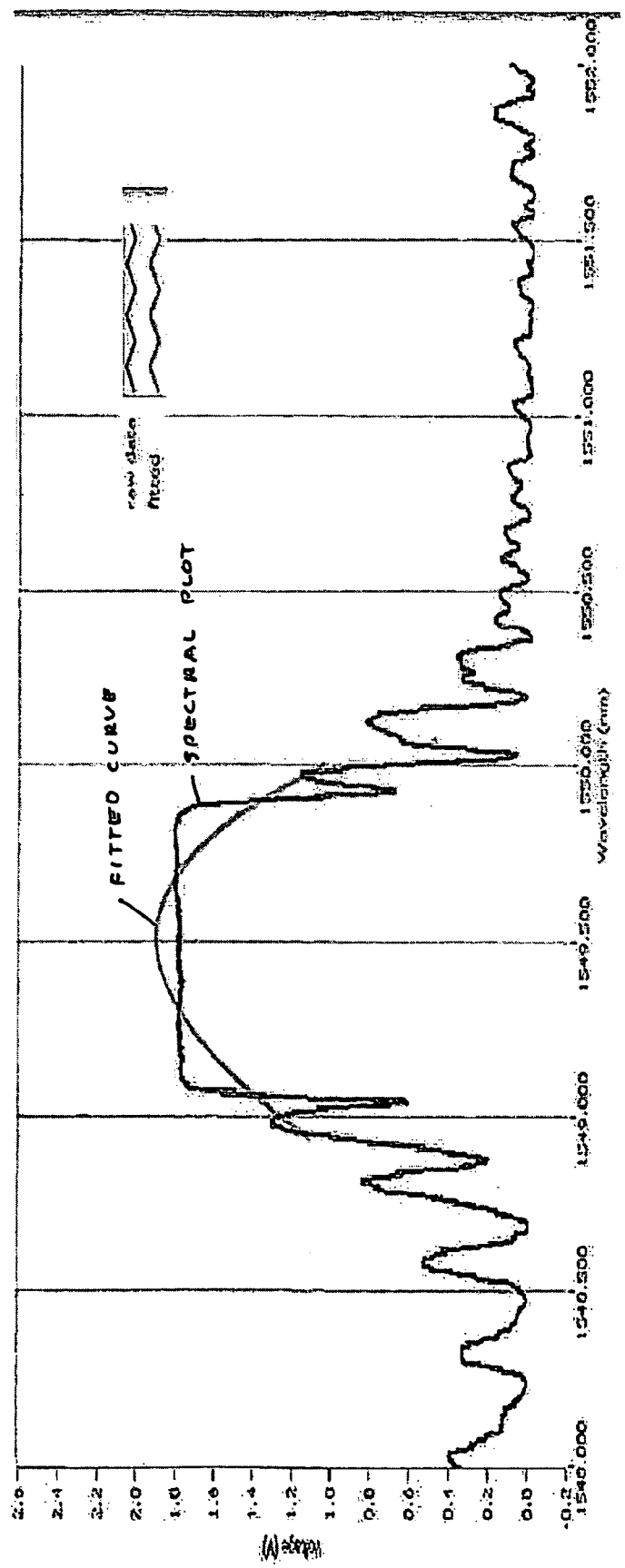
FIG. 12 is a plot showing a reflection curve and a fitted curve using the present invention.

FIG. 12 shows an exemplary fitted curve from an exemplary spectral plot using the above procedure.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

What is claimed is:

1. A hyperthermia therapy system comprising;
an electromagnetic radiation source adapted to cause increase of the temperature of a selected tissue area upon exposure to the electromagnetic radiation for hyperthermia therapy;
a temperature profiling portion of the system for measuring temperature changes caused by the electromagnetic radiation comprising;
   an optical fiber temperature sensor comprising a series of FBGs spaced apart along an optical fiber sensor element, each FBG having a different reflection spectrum and a different specified characteristic peak wavelength adapted to be placed adjacently proximate tissue whose temperature is to be determined and monitored during hyperthermia treatment;
   an interrogation portion coupled to the optical fiber temperature sensor comprising a scanning light source having a scanning rate defining scan cycles to send interrogating light to the optical fiber sensor, the scanning light source having a scanning wavelength range sufficiently broad to cause reflection by all of the FBGs such that each scanning cycle updates the reflection spectra of the FBGs;
a detection and processing portion for detecting the reflected light of the FBGs and determining therefrom the temperature and the temperature change locally to each FBG comprising;
   a wavelength selective detector element coupled to receive reflected light from the FBGs and operative at a sampling rate to produce a time division electrical signal representative of the spectra reflected from each FBG;
   a specially programmed processor in communication with the wavelength selective detector element to control its sampling rate and to convert the time divisions of the time division electrical digital signal to wavelength divisions and to identify wavelength peaks for each FBG in each of said scanning cycles by applying a curve smoothing and curve fitting and peak detection
procedure comprising;
   sampling the signal at a sampling rate defined by:

$$\frac{\text{light source scanning rate}}{\text{desired temperature resolution} \times Kt};$$

applying the sampling rate to the wavelength selective detector;
defining a bin for each FBG in which each bin has a lower wavelength limit and an upper wavelength limit which is not more than ½the difference between the specified characteristic peak wavelength of the FBG and the specified characteristic peak wavelength of the next lower and the next higher FBG, respectively;
in each bin selecting a number of data points over which to smooth thereby creating a smoothing window having N data points;
replacing each of the data points in each smoothing window by the mean value of the set of data points consisting of N/2 data points preceding the data point and N/2 data points succeeding the data point defining a second set of data points;

curve fitting the second set of data points to a polynomial curve of order of at least two;

determining the peak of the polynomial curve to define a wavelength peak of each FBG;

taking the difference of the wavelength peak of each FBG at selected time intervals from a predetermined wavelength peak at a base condition and converting that wavelength difference to a temperature difference by multiplying by Kt; and an output device adapted to provide a temperature profile at each of the selected time intervals comprising the temperature at each FBG and /or the temperature change at each FBG.

* * * * *